United States Patent [19]
Noteboom

[11] 3,941,661
[45] Mar. 2, 1976

[54] ROLLER CULTURE BOTTLE INSERT
[75] Inventor: William D. Noteboom, Columbia, Mo.
[73] Assignee: The Curators of the University of Missouri, Columbia, Mo.
[22] Filed: Jan. 16, 1974
[21] Appl. No.: 433,686

[52] U.S. Cl................................. 195/127; 195/1.7
[51] Int. Cl.²........................................... C12K 9/00
[58] Field of Search ............ 195/127, 1.8; 261/101, 261/103; 219/497

[56] References Cited
UNITED STATES PATENTS
3,633,753  1/1972  Petitjean............................ 210/497
3,695,443  10/1972  Schmidt............................. 210/497
3,740,321  6/1973  Pagano et al. ..................... 195/127

Primary Examiner—Alvin E. Tanenholtz
Attorney, Agent, or Firm—Ray E. Snyder

[57] ABSTRACT

A plastic spiral insert for use in existing roller culture bottles effective to increase the total surface area available for cell culture. The insert consists of a continuous coil of plastic sheet material that may be thermally set so as to retain its spiral configuration within the roller bottle and may also include integral raised portions on the sheet material effective to maintain uniform spacing between successive layers of the coil. The invention also includes retraction apparatus for removing the insert from small necked bottles.

5 Claims, 8 Drawing Figures

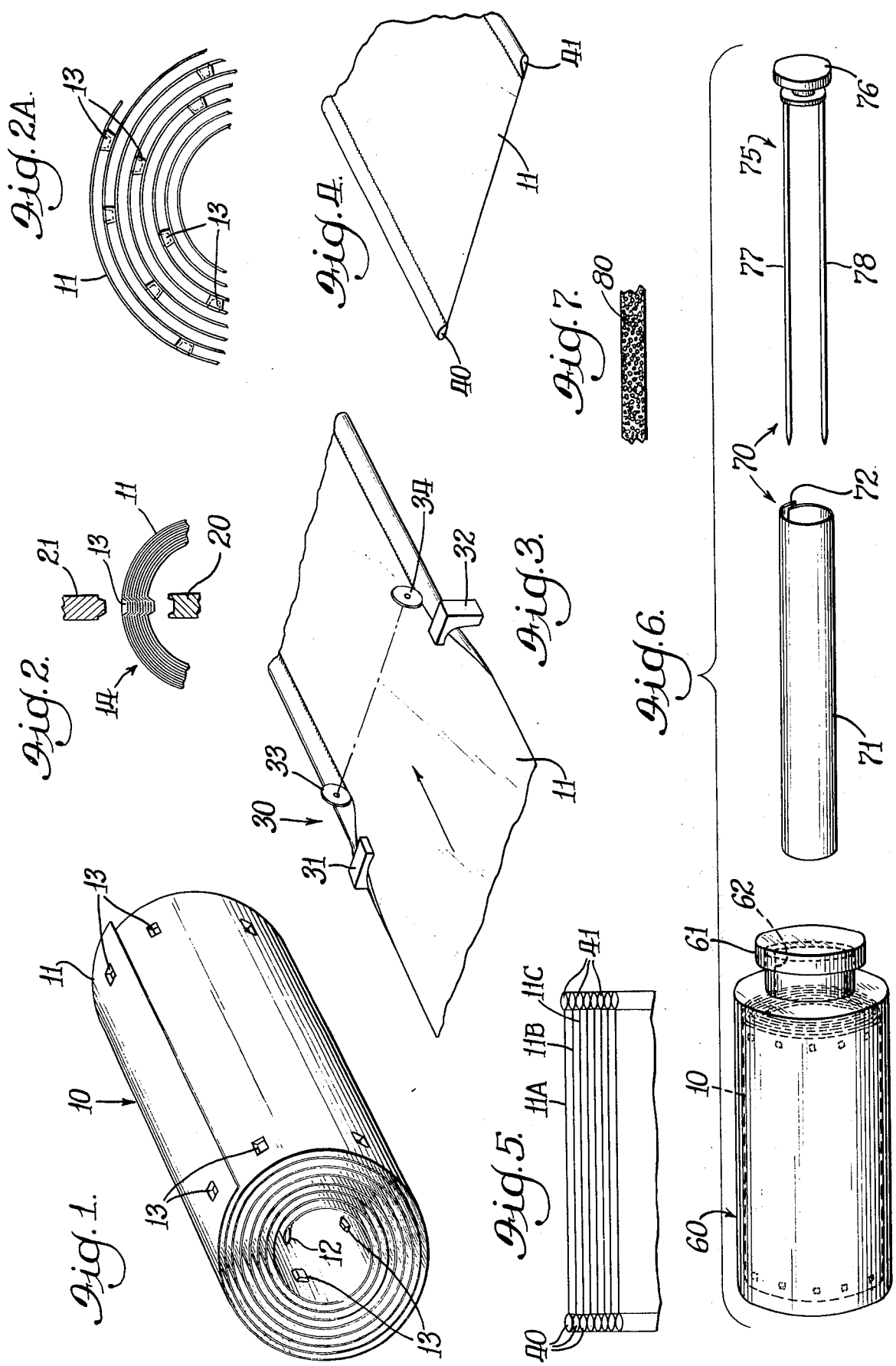

ROLLER CULTURE BOTTLE INSERT

BACKGROUND OF THE INVENTION

1. Field of the Invention

The invention relates generally to fermentation chemistry, and more particularly to apparatus for propagating or fermenting including submergers, agitators, circulators or dispersers.

2. Description of the Prior Art

The use of roller tubes and bottles for the cultivation of microorganisms and cells, particularly anchorage dependent cells, is well known in the art. A machine for rolling culture tubes is shown in the patent to McBee, U.S. Pat. No. 3,338,795.

More sophisticated apparatus for the cultivation of microorganisms is shown in the patent to Monod, U.S. Pat. No. 2,686,754. The apparatus of Monod includes a rotary drum that is partially filed with culture medium and is disposed to rotate about a horizontal axis. The drum is formed on its interior with a continuous spiral rib which passes through the medium and on which a liquid film is formed. This provides for the required aeration of the liquid without the formation of foam, such as might be formed when air is bubbled through the medium. Aeration by bubbling commonly does produce foam which requires the addition of a surfactant to suppress. The addition of any foreign element to the culture medium is not desirable.

Another method for bulk culture of animal cells on plastic film is described in Experimental Cell Research 71 (1972) 293–296, by W. House, Moira Shearer and N. G. Maroudas. Their apparatus includes a roller bottle with a spiral interior film, the successive coils of which are separated by corrugated film. The bottle is rolled in a horizontal plane to obtain cell adherence and then set erect in a vertical plane to bubble air through the medium. Their bottle requires an opening equal to the diameter of the bottle in order to admit the spiral film.

SUMMARY OF THE INVENTION

It is an object of the present invention to provide a collapsible spiral insert for use in a roller culture bottle whereby the effective surface area available for the growth of cells and microorganisms is increased several fold.

It is a more particular object to provide a spiral insert in the form of a continuous coil of plastic sheet material that may be thermally set so as to retain its spiral configuration within the culture bottle when in contact with a warm culture medium.

It is a still more particular object to provide an insert of the type described that is formed with integral bosses or dimples that are effective to maintain uniform spacing between successive layers of the coil. The raised bosses or dimples preferrably are formed when the insert is tightly coiled or are otherwise formed so as to inter-nest when the spiral is tightly coiled so as to permit easy insertion into the relatively small neck of a culture bottle.

It is another object to provide an altermative form of insert in the form of a continuous coil of plastic sheet material formed with a continuous loop or bead along one or both edges. The loops being collapsible for tightly coiling the spiral insert and being effective to provide uniform spacing between layers of the coil in an operable condition. The continuous bead also functions to contain the culture medium on the surface of the sheet between successive layers.

It is also an object of the invention to provide apparatus for the retraction of the spiral insert from a culture bottle which includes a rigid metal or plastic tube formed with a longitudinal slot and an elongated fork operable to engage a leading edge of the spiral insert for winding the insert into the tube.

BRIEF DESCRIPTION OF THE DRAWINGS

FIG. 1 is a perspective view of the plastic spiral insert of the present invention;

FIG. 2 is a fragmentary view of the tightly coiled insert of FIG. 1;

FIG. 2A shows a portion of the spiral in expanded form;

FIG. 3 is a perspective schematic view of apparatus for forming loops on the edges of the spiral sheet material FIG. 4 is a fragmentary perspective view of the plastic sheet material with completed loops;

FIG. 5 is a partial sectional view showing the sheet material of FIG. 4 in coiled form;

FIG. 6 is an exploded view of a roller culture bottle and apparatus for retracting the spiral insert from the bottle; and FIG. 7 is a fragmentary view of an alternative form of plastic sheet material.

DESCRIPTION OF THE PREFERRED EMBODIMENT

The plastic spiral insert of the present invention is shown in perspective form in FIG. 1 and is designated generally by the numeral 10. The insert preferably is formed of a continuous sheet 11 of thermal setting plastic material. The material of the sheet 11 should be relatively inert chemically and should be capable of retaining a thermal set under relatively high temperatures, as in a steam autoclave, for example. However, it is intended that the insert described may be inexpensive enough to be disposable after one use if desired.

I have found that sheet Mylar of a thickness of 10 to 40 mils is suitable for most applications. Some variation in thickness or number of turns may be desired to accommodate different size bottles or different culture media. The surface of the sheet 11 may also be treated or coated with a suitable material to aid cell adherence, as by ionic attraction.

The spiral insert 10 is formed in one embodiment by winding the sheet of plastic 11 into a continuous coil on a suitable form, heating it to a temperature where it begins to soften so that internal stresses are relieved, and then cooling it so that it takes a "set" in the form of the desired expanded spiral. The insert 10 is collapsed into a tight coil of small diameter for packaging or for insertion into the neck of a roller bottle, such as the bottle 60 shown in FIG. 6. After the insert 10 is passed through the neck of the bottle, it expands to the shape in which it was thermally set. It is desirable that the expanded form of the spiral closely match the internal diameter of the roller bottle for which it is intended. This is to ensure that the insert 10 rotates with the bottle and does not float in the culture medium. If the expanded form of the insert 10 greatly exceeds the internal diameter of the roller bottle, the outer layers of the spiral 10 may be compressed together too closely to allow free passage of the culture medium therebetween.

The sheet 11 of plastic may be formed at its inner leading edge with a loop or bead 12 to facilitate easy recoiling of the spiral 10. The loop 12 may be formed by folding the leading edge over on itself and heat sealing, or by bonding with a suitable adhesive. Other devices may also be attached to the leading edge for this purpose.

Uniform radial spacing of successive layers of the spiral insert 10 can be obtained by preforming the sheet 11 with a plurality of dimples or depressions 13 of the desired depth. Preformed raised bosses might also be provided for the same purpose. The desired spacing may not be the same for all applications, depending on the viscosity and wettability of the culture medium.

A method for forming the depressions 13 or bosses on the plastic sheet 11 is shown in FIG. 2. The sheel 11 is first collapsed into a tight coil 14. One member 20 of a forming die is inserted into the center 15 of the coil 14. The other member 21 of the forming die is then pressed into contact with the coil 14 against the die member 20. In this manner, the depressions 13 are stacked or nested when the spiral 10 is tightly coiled. When the spiral 10 is allowed to expand to its pre-set size, the depressions 13 are staggered, as shown in FIG. 2A, and act as spacers between successive layers. The dimples 13 formed may be of a depth (or height) as to provide a spacing between layers of as little as 1 or 2 millimeters. When the spiral 10 is recoiled, the depressions 13 are again nested to allow a tight coil 14 to be formed. The plastic sheet 11 has enough flexibility to allow the dimples 13 to fall into place.

An alternative method of preforming the plastic sheet 11 is shown in FIGS. 3, 4 and 5. In this method, the sheet 11 is passed through a machine 30 for forming beads or loops 40 and 41 on the edges of the sheet 11. The machine 30 comprises a pair of forming blocks 31 and 32, and a pair of heat sealing rollers 33 and 34. The blocks 31 and 32 may be heated to facilitate the folding over of the edges of the sheet 11. The sealing rollers 33 and 34 bond the edges upon the sheet 11 to form the continuous loops or beads 40 and 41, as shown in FIG. 4.

The loops 40 and 41 are compressible, and when the sheet 11 is wound into a spiral 50, as shown in FIG. 5, these loops act as spacers for successive layers 11A, 11B, 11C, etc. The loops 40 and 41 are also compressible enough to allow the spiral 50 to be collapsed into a tight coil for insertion into the neck of a culture bottle. The loops also serve to keep the culture medium on the surface of the sheet 11 by preventing flow off the edges. Thermal setting of the spiral 50 in this embodiment may be unnecessary.

Apparatus 70 for retracting a spiral 10 from a culture bottle 60 is shown in FIG. 6. The apparatus 70 comprises a rigid metal or plastic tube 71 formed with a tangentially opening longitudinal slot 72, and a fork 75 formed with a knob or handle 76 and a pair of elongated tines 77 and 78. The tube 71 is inserted through the neck 61 of the bottle 60 with the slot 72 engaging the leading inner edge 12 of the spiral 10. The fork 75 is then inserted so that one tine of the fork 75 engages the loop 12 on the leading edge 12. By holding the tube 71 stationary, the knob 76 is then turned winding the spiral 10 within the tube 71. When the spiral 10 is completely wound within the tube 71, the tube is removed from the bottle. It is preferable that the length of the tube 71 be greater than the depth of the bottle 60.

In operation, the spiral insert 10 is utilized in a culture bottle 60 as follows:

The spiral 10 is first sterilized and then collapsed into a tight coil 14 and inserted through the neck of a sterile bottle 60. The coil 14 expands to its normal size filling the bottle 60. The bottle 60 is set upright and a volume of medium containing a certain number of cells is added. The cap 62 is attached to the bottle 60 and the bottle is then rotated rapidly by hand to distribute the medium and cells over the surface of the spiral 10. The bottle 60 is then placed on a rolling machine and caused to rotate slowly about a horizontal axis. The slow rotation of the spiral 10 through the medium provides the necessary aeration for cell growth and multiplication.

When the cell growth has reached a desired stage, the medium is removed from the bottle 60 and the cells are removed from the spiral 10 surface. The cells may be removed by the conventional means of trypsinization, either with the spiral 10 still within the bottle 60 or after the spiral 10 has been removed from the bottle.

It should be noted that the use of the spiral 10 in a culture bottle 60 having a relatively small neck permits the filling of the bottle 60 with culture media to a greater depth than one layer of the spiral.

It should also be noted that the spiral 10 herein defined might be used to advantage in existing perfusion culture flasks in order to provide a continuous exchange of medium, if so desired.

The invention may be still further improved by the substitution of an open porous plastic material 80 (shown in FIG. 7) for the smooth solid Mylar sheet 11. Such a porous sheet material 80 might be composed of high density polyethylene in a form supplied by the Porex Materials Corp. of Fairburn, Ga. Other porous sheet material, such as polystyrene may also be used in this application.

I have found that the cells growing on such a porous structure are effectively lifted off in the presence of a trypsin solution. In this embodiment, the total cell growth thus is multiplied severalfold, first due to the multiple layers of the spiral, and secondly due to the increased surface area provided by the porous structure.

It is to be understood that many modifications can be made to the embodiments shown and described without departing from the spirit of the invention. The invention is not to be considered as limited to the embodiments described herein except in-so-far as the claims may be so limited.

I claim:

1. Apparatus for use in a roller culture bottle that is partially filled with a culture medium for the growing of cells or microorganisms and comprising:

a continuous elongated sheet of plastic material wound into a tight cylindrical coil and thermally set so as to retain a spiral configuration for insertion into the culture bottle and further adapted to expand into an enlarged spiral configuration after insertion into the bottle, and spacing means formed integrally with said sheet for separating successive layers of said spiral when present within the culture bottle so as to permit the passage of culture medium therethrough as the bottle is rolled about an axis coincident with the axis of said spiral.

2. The apparatus of claim 1 wherein, said sheet of plastic material is formed with a plurality of integral raised bosses, each adapted to contact a successive layer of said spiral for maintaining a uniform spacing between successive layers.

3. The apparatus of claim 1 wherein,
said sheet of plastic material is formed on at least one edge with a continuous integral loop.

4. The apparatus of claim 1 wherein,
said sheet of plastic material is comprised of open porous material.

5. The apparatus of claim 1 wherein,
said sheet of plastic material is formed on its inner leading edge with integral engagement means to facilitate removal of said sheet from the bottle.

* * * * *